(12) United States Patent
Vetter et al.

(10) Patent No.: US 7,331,941 B2
(45) Date of Patent: Feb. 19, 2008

(54) PREFILLED HYPODERMIC SYRINGE

(75) Inventors: Udo J. Vetter, Ravensburg (DE); Andreas Schütz, Krailling (DE); Joachim Glocker, Weingarten (DE)

(73) Assignee: Arzneimitiel GmbH Apotheker Vetter & Co. Ravensburg, Ravensburg (DE)

( * ) Notice: Subject to any disclaimer, the term of this patent is extended or adjusted under 35 U.S.C. 154(b) by 201 days.

(21) Appl. No.: 10/821,253

(22) Filed: Apr. 8, 2004

(65) Prior Publication Data
US 2005/0027259 A1   Feb. 3, 2005

(30) Foreign Application Priority Data
Apr. 9, 2003   (DE) ................ 103 16 127

(51) Int. Cl.
*A61M 5/32* (2006.01)
*A61M 5/00* (2006.01)

(52) U.S. Cl. ............... 604/192; 604/163; 604/263

(58) Field of Classification Search ............ 604/192, 604/198–201, 263, 403, 411–413, 415, 187, 604/164.08, 197, 163, 232, 234, 171, 181; 128/919; 206/363–365
See application file for complete search history.

(56) References Cited

U.S. PATENT DOCUMENTS

| | | | |
|---|---|---|---|
| 5,447,500 A * | 9/1995 | Bergstresser et al. ........ 604/198 |
| 5,624,405 A * | 4/1997 | Futagawa et al. ............ 604/199 |
| 5,879,337 A * | 3/1999 | Kuracina et al. ............ 604/192 |
| 6,186,980 B1 * | 2/2001 | Brunel ........................ 604/110 |

* cited by examiner

*Primary Examiner*—Matthew DeSanto
(74) *Attorney, Agent, or Firm*—Andrew Wilford

(57) ABSTRACT

A hypodermic syringe has a hollow body adapted to hold a liquid, an inner cap fitted over an end of the body, and an axially extending needle seated in the inner cap and having an outer point projecting axially outward from the inner cap and an inner point projecting axially inward from the inner cap toward the body. An outer cap fittable over the inner cap and needle is connected to a clamp ring engageable around the inner cap by a frangible web. Interengaging formations on the ring and on the inner cap releasably retain the outer cap in an outer position spaced axially outward of the body and in which an interior of the outer cap is open to the exterior and an inner position spaced axially closely to the body and in which the interior of the outer cap is not open to the exterior.

4 Claims, 1 Drawing Sheet

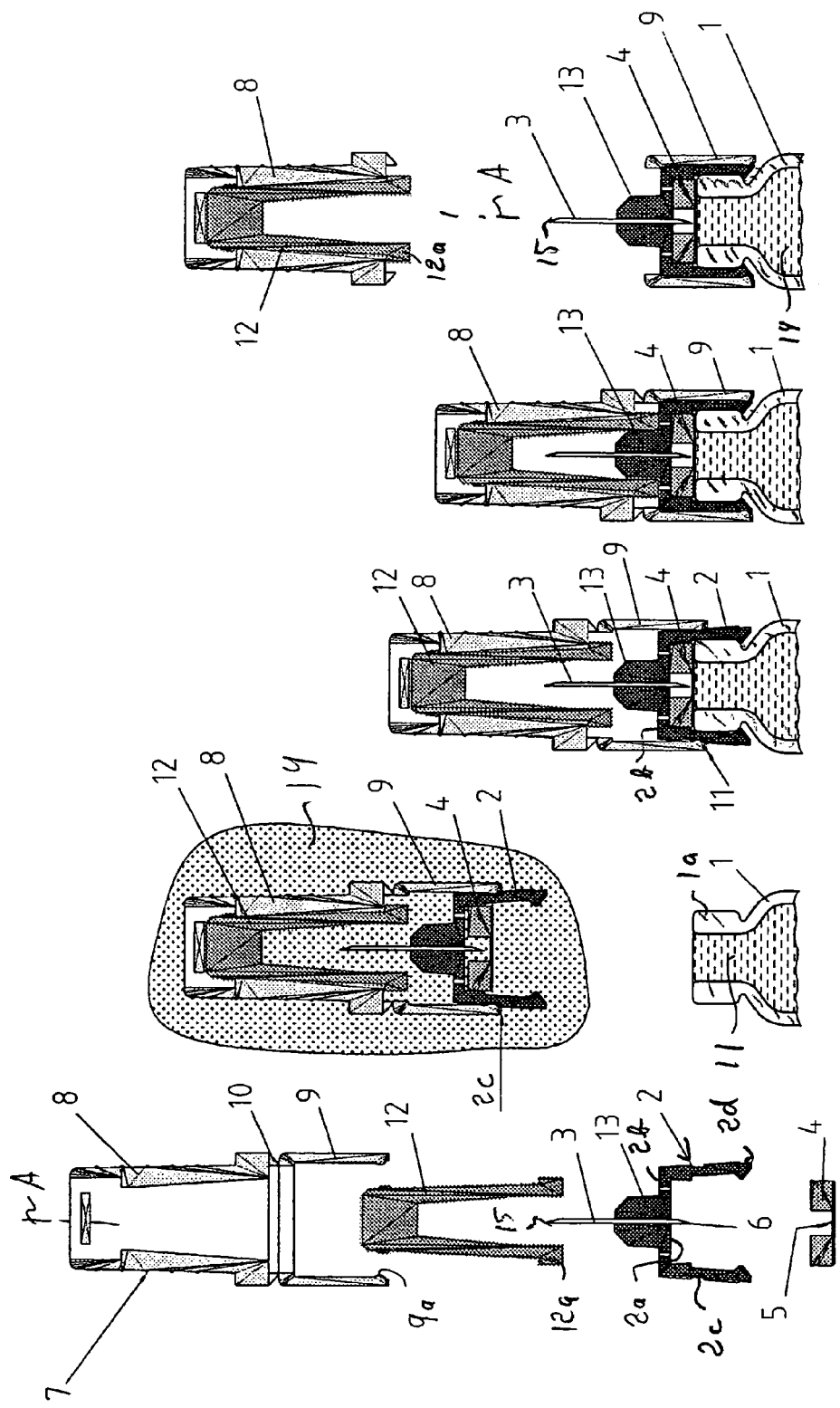

PREFILLED HYPODERMIC SYRINGE

FIELD OF THE INVENTION

The present invention relates to a hypodermic syringe. More particularly this invention concerns such a syringe that is prefilled.

BACKGROUND OF THE INVENTION

A standard hypodermic syringe comprises a hollow body holding a liquid medicament and a piston. An open end of the body carries an inner cap in which is seated a needle so that, when the piston is advanced, the liquid is expressed through the needle.

In order to maintain sterility before use, especially when the syringe is supplied prefilled to the user, it is standard to provide a protector cap over the needle. This cap is removed before use.

The manufacture of such a syringe is fairly complex, in particular because the needle and outer end of the assembly must be maintained sterile. Thus during assembly it is necessary to provide several sterilizing steps as the various parts are fitted together. This manufacture is even more complex when high-temperature sterilization is required.

OBJECTS OF THE INVENTION

It is therefore an object of the present invention to provide an improved hypodermic syringe and method of manufacturing same.

Another object is the provision of such an improved hypodermic syringe and method of manufacturing same which overcome the above-given disadvantages, that is which produce a perfectly sterile prefilled syringe in a few simple steps.

SUMMARY OF THE INVENTION

A hypodermic syringe has according to the invention a hollow body adapted to hold a liquid and having an axially outwardly open end, an inner cap fitted over the body end, an axially extending needle seated in the inner cap and having an outer point projecting axially outward from the inner cap and an inner point projecting axially inward from the inner cap toward the body, and a washer between the inner cap and the body end having a central hole into which the inner point of the needle engages and provided with a membrane closing the hole and spaced axially inward from the inner point. An outer cap fittable over the inner cap-and needle is connected to a clamp ring engageable-around the inner cap by a frangible web. Interengaging formations on the ring and on the inner cap releasably retain the outer cap in an outer position spaced axially outward of the body and in which an interior of the outer cap is open to the exterior and an inner position spaced axially-closely to the body and in which the interior of the outer is not open to the exterior.

According to the invention the glass body can be subjected to high-temperature processes, e.g. siliconizing, before it is filled. In addition the membrane keeps the needle dry and out of contact with liquid medicament, so any reaction between the medicament and the metallic needle prior to use is impossible. Furthermore, the membrane is automatically pierced when the piston of the body is first advanced, since it will deform axially outward against the inner point of the needle.

Thus according to the invention after cleaning and filling the body, the inner cap and washer are mounted in place. The outer cap is fitted by its clamp ring to the inner cap in the outer position and the assembly is sterilized by a gaseous agent, e.g. hot air. Then the outer cap is pushed down to lock it in the inner position, in which in fact the formations secure the clamp ring so solidly to the inner cap that the web will fracture before the ring releases from the inner cap. For use the outer cap is snapped off the inner cap, exposing the outer point of the needle. Pressurization of the contents of the syringe forces the membrane against the inner point of the needle and punctures this membrane so the liquid can flow out through the needle.

According to the invention a liner cup is provided inside the outer cap, receiving the outer point of the needle, and clamped in the inner position between the outer cap and the inner cup. This cup is of rubber or a good-sealing elastomer. The inner cap is formed with a central outwardly extending projection from which the needle extends axially outward and that fits snugly in the liner cup in the inner position.

The body is normally cleaned and siliconized before is filled. In addition the body is filled without bubbles or air inclusions.

BRIEF DESCRIPTION OF THE DRAWING

The above and other objects, features, and advantages will become more readily apparent from the following description, reference being made to the accompanying drawing in which:

FIG. 1 is an exploded sectional view of a syringe according to the invention;

FIGS. 2, 3, and 4 are sections like FIG. 1 of the syringe in succeeding stages of assembly; and FIG. 5 is a section showing the syringe when ready for use.

SPECIFIC DESCRIPTION

As seen in the drawing, a standard syringe has a glass carpule or body 1 intended to hold a liquid medicament 11 and having as is well known in the art an unillustrated plunger and a neck 1a centered on an axis A of the body 1. An inner cap 2 of a somewhat flexible plastic fits snugly over this neck 1a and has a central axially outwardly extending projection 13 in which is seated a standard double-pointed needle 3 having an inner end or point 6 projecting axially inward slightly past an inner face 2a of the inner cap 2 and an outer point 15. A ring 9 is formed with radially inwardly projecting bumps 9a that can engage in an outwardly open groove 2c of the inner cap 2 or in another groove 2d at the inner edge of this cap 2 as will be described below. An elastomeric washer 4 fits between the inner face 2a and the neck 1a and has at its inner face an elastic membrane 5 that is spaced in the assembled condition from the point 6.

A protector 7 centered on the axis A comprises a hard-plastic outer cap 8, the clamp ring 9 that can be formed by a plurality of axially extending arms separated by axially downwardly open slots, and a frangible web or weakened region 10 connecting the ring 9 to the outer cap 8. A soft rubber liner cup 12 fits inside the outer cap 8 and has a rim 12a that can sit sealingly on an annular outer face 2b of the inner cap 2 around the projection 13.

As a first step, the body 1 is cleaned, siliconized, and filled without bubbles with the liquid medicament 11.

Then as shown in FIG. 2 the liner cup 12 is fitted in the outer cap 8, the washer 4 is fitted inside the inner cap 2, and the bumps 9a of the ring 9 are fitted to the outer formation constituted by the groove 2c. In this position the rim 12a of the cup 12 is spaced from the end face 2b of the inner cap 2 so that the interior of the protector 7 and liner cup 12 is open to the exterior and a hot sterilizing gas as indicated at 14 can flood it and reach all critical interior surfaces.

This subassembly of the protector 7, cup 12, inner cap 2, and washer 4 is then fitted as shown in FIG. 3 to the syringe, in which case the inner cap 2 snaps snugly in place over the neck 1a of the filled syringe body 1. Sterilizing can continue or be repeated in this position, since so long as the protector 7 is in the upper position its interior surfaces can be reached by the hot sterilizing gas 14.

Finally as shown in FIG. 4 the assembly is completed by pushing the outer cap 8 down on the inner cap 2 so the bumps 9a of the ring 9 move from the outer groove 2c to the inner groove 2d. In this position the rim 12a of the liner cup 12 sits flatly on the outer face 2b of the cap 2 and snugly around the projection 13, thereby isolating the outer portion of the needle 3 in a sterilized closed space. Once in this position the assembly can be handled without contamination, as the critical surfaces are wholly contained.

For use as shown in FIG. 5 the outer cap 8 of the protector 7 is snapped off the ring 9 by twisting or tipping it so as to fracture the web 10. Axially forwardly advancing the unillustrated piston in the body 1 will pressurize the liquid 11 and thereby deform the membrane 5 so it moves outward and is punctured by the inner point 6 of the needle 3, allowing the liquid 11 to exit through the needle 3

We claim:

1. A hypodermic syringe comprising:
    a hollow body adapted to hold a liquid and having an axially outwardly open end;
    an inner cap fitted over the body end;
    an axially extending needle seated in the inner cap and having an outer point projecting axially outward from the inner cap and an inner point projecting axially inward from the inner cap toward the body;
    a washer between the inner cap and the body end, having a central hole into which the inner point of the needle engages, and provided with a membrane closing the hole and spaced axially inward from the inner point and out of engagement with the needle;
    an outer cap fittable over the inner cap and needle;
    a clamp ring engageable around the inner cap;
    a frangible web connecting the ring to the outer cap; and
    interengaging formations on the ring and on the inner cap for releasably retaining the outer cap in an outer position spaced axially outward of the body and in which an interior of the outer cap is open to the exterior and an inner position spaced axially closely to the body and in which the interior of the outer cap is not open to the exterior.

2. The hypodermic syringe defined in claim 1, further comprising
    a liner cup inside the outer cap, receiving the outer point of the needle, and clamped in the inner position between the outer cap and the inner cap.

3. The hypodermic syringe defined in claim 2 wherein the liner cup is of rubber.

4. The hypodermic syringe defined in claim 2 wherein the inner cap is formed with a central outwardly extending projection from which the needle extends axially outward and that fits snugly in the liner cup in the inner position.

* * * * *